US00PP32048P2

(12) United States Plant Patent
Head et al.

(10) Patent No.: US PP32,048 P2
(45) Date of Patent: Aug. 11, 2020

(54) ***THUJA* TREE NAMED 'RLH-GG'**

(50) Latin Name: ***Thuja standishii* x *Thuja plicata***
Varietal Denomination: RLH-GG

(71) Applicants: Robert Harold Head, Seneca, SC (US); Lisa Jones Head, Seneca, SC (US)

(72) Inventors: Robert Harold Head, Seneca, SC (US); Lisa Jones Head, Seneca, SC (US)

(73) Assignee: Head's Select Inc., Seneca, SC (US)

( * ) Notice: Subject to any disclaimer, the term of this patent is extended or adjusted under 35 U.S.C. 154(b) by 0 days.

(21) Appl. No.: 16/501,898

(22) Filed: Jul. 1, 2019

(51) Int. Cl.
*A01H 7/00* (2006.01)

(52) U.S. Cl.
USPC ..... Plt./213

(58) Field of Classification Search
USPC ..... Plt./213
CPC ..... A01H 7/00
See application file for complete search history.

*Primary Examiner* — Keith O. Robinson
(74) *Attorney, Agent, or Firm* — C. A. Whealy

(57) ABSTRACT

A new and distinct cultivar of *Thuja* tree named 'RLH-GG', characterized by its relatively compact, upright and narrowly columnar plant form; moderately vigorous growth habit and moderate growth rate; freely branching habit; dense and bushy form from base to top of the tree; lateral branches that are fine-textured and flexible and resist cracking and splitting; dark green-colored leaves that are soft and fine-textured and tolerate high humidity and high temperatures conditions; and good garden performance.

1 Drawing Sheet

Botanical designation: *Thuja standishii* x *Thuja plicata.*
Cultivar denomination: 'RLH-GG'.

BACKGROUND OF THE INVENTION

The present invention relates to a new and distinct cultivar of *Thuja* tree, botanically known as *Thuja standishii* x *Thuja plicata* and hereinafter referred to by the name 'RLH-GG'.

The new *Thuja* tree is a naturally-occurring branch mutation of *Thuja standishii* x *Thuja plicata* 'Green Giant', not patented. The new *Thuja* tree was discovered and selected on a single plant in 2005 by the Inventors from within a population of trees of 'Green Giant' grown in an outdoor nursery environment in Long Creek, Oconee County, S.C.

Asexual reproduction of the new *Thuja* tree by semi-hardwood and hardwood cuttings in a controlled environment in Seneca, Oconee County, S.C. since 2010, has shown that the unique features of this new *Thuja* tree are stable and reproduced true to type in successive generations.

SUMMARY OF THE INVENTION

Trees of the new *Thuja* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'RLH-GG'. These characteristics in combination distinguish 'RLH-GG' as a new and distinct *Thuja* tree:

1. Relatively compact, upright and narrowly columnar plant form.
2. Moderately vigorous growth habit and moderate growth rate.

3. Freely branching habit; dense and bushy form from base to top of the tree.
4. Lateral branches that are fine-textured and flexible and resist cracking and splitting.
5. Dark green-colored leaves that are soft and fine-textured and tolerate high humidity and high temperatures conditions.
6. Good garden performance.

Trees of the new *Thuja* can be compared to trees of the mutation parent, 'Green Giant'. Trees of the new *Thuja* differ primarily from trees of 'Green Giant' in the following characteristics:

1. Trees of the new *Thuja* are relatively compact, dense and have a narrowly columnar plant form whereas trees of 'Green Giant' are larger, more open and have a broad pyramidal plant form.
2. Trees of the new *Thuja* are less vigorous and grow slower than trees of 'Green Giant'.
3. Leaves of trees of the new *Thuja* are softer, finer-textured and more tolerant to low temperatures than leaves of trees of 'Green Giant'.

Trees of the new *Thuja* can be compared to trees of *Thuja plicata*, 'Altrovirens', not patented. In side-by-side comparisons, trees of the new *Thuja* differ primarily from trees of 'Altrovirens' in the following characteristics:

1. Trees of the new *Thuja* are relatively compact, dense and have a narrowly columnar plant form whereas trees of 'Altrovirens' are larger, more open and have a broader pyramidal plant form.
2. Trees of the new *Thuja* grow slower than trees of 'Altrovirens'.
3. Lateral branches of trees of the new *Thuja* are finer-textured and more flexible than lateral branches of trees of 'Altrovirens'.

4. Leaves of trees of the new *Thuja* are softer, finer-textured and more tolerant to low temperatures than leaves of trees of 'Altrovirens'.

BRIEF DESCRIPTION OF THE PHOTOGRAPH

The accompanying colored photograph illustrates the overall appearance of the new *Thuja* tree showing the colors as true as it is reasonably possible to obtain in colored reproductions of this type. Colors in the photograph may differ slightly from the color values cited in the detailed botanical description which accurately describe the colors of the new *Thuja* tree.

The photograph is a side perspective view of a typical tree of 'RLH-GG' grown in a container.

DETAILED BOTANICAL DESCRIPTION

The aforementioned photograph and following observations, measurements and values describe trees grown during the winter in #7 nursery containers in an outdoor nursery in Park Hill, Okla. and under cultural practices typical of commercial *Thuja* tree production. During the production of the trees, day temperatures ranged from −10° C. to 45° C. and night temperatures ranged from −26° C. to 35° C. Trees used in the photograph and for the description were four years old. In the following detailed description, color references are made to The Royal Horticultural Society Colour Chart, 2007 Edition, except where general terms of ordinary dictionary significance are used.

Botanical classification: *Thuja standishii* x *Thuja plicata* 'RLH-GG'.

Parentage: Naturally-occurring branch mutation of *Thuja standishii* x *Thuja plicata* 'Green Giant', not patented.

Propagation:

*Type*.—By semi-hardwood and hardwood cuttings.

*Time to produce rooted young trees, winter*.—About 120 to 180 days at temperatures ranging from 8° C. to 17° C.

*Root description*.—Fine to medium in thickness; fibrous.

*Rooting habit*.—Freely branching; dense.

*Root color*.—Developing roots, close to 155B; developed roots, close to 166C to 166D.

Tree description:

*Tree and growth habit*.—Woody ornamental evergreen tree; relatively compact, upright and narrowly columnar plant form; moderately vigorous growth habit and moderate growth rate; freely branching habit; dense and bushy form from base to top of the tree.

*Tree height*.—About 1.75 meters to 2 meters.

*Tree diameter, base*.—About 50 cm to 60 cm.

*Lateral branch description*.—Branching habit and description: Freely branching habit; branches are upright to outwardly; lateral branches are fine-textured and flexible and resist cracking and splitting. Length: About 3 cm to 14 cm. Diameter: About 1.5 mm to 3 mm. Internode length: About 5 mm to 20 mm. Strength: Strong, flexible. Texture, developing branches: Smooth, glabrous. Texture, trunk: Scaly vertical strips; underneath outer bark, smooth and glabrous. Color, developing branches: Close to 137A and N137D. Color, developed branches: Close to 175B.

*Leaf description*.—Appearance and arrangement: Flattened and closely appressed, scale-like; opposite to whorled, simple; sessile. Length: About 1 mm to 2.5 mm. Width: About 0.5 mm to 1.5 mm. Shape: Scale-like. Apex: Minutely aristulate. Base: Broadly obtuse. Margin: Entire; not undulate. Venation pattern: Parallel. Texture: Smooth, glabrous; soft and flexible. Color: Developing leaves, upper surface: Close to 137A to 137B. Developing leaves, lower surface: Close to 146A to 146B. Fully expanded leaves, upper surface: Close to between 137A to N137D; venation, close to between 137A to N137D. Fully expanded leaves, lower surface: Close to 137A; venation, close to 137A.

Cone description: To date, cone development has not been observed on trees of the new *Thuja*.

Landscape performance: To date, trees of the new *Thuja* have been observed have good landscape performance, good winter hardiness and to tolerate wind, high humidity and temperatures ranging from about −26° C. to about 45° C.

Pathogen & pest resistance: To dale, trees of the new *Thuja* have not been observed to be resistant to pathogens and pests common to *Thuja* trees.

It is claimed:

1. A new and distinct *Thuja* tree named 'RLH-GG' as illustrated and described.

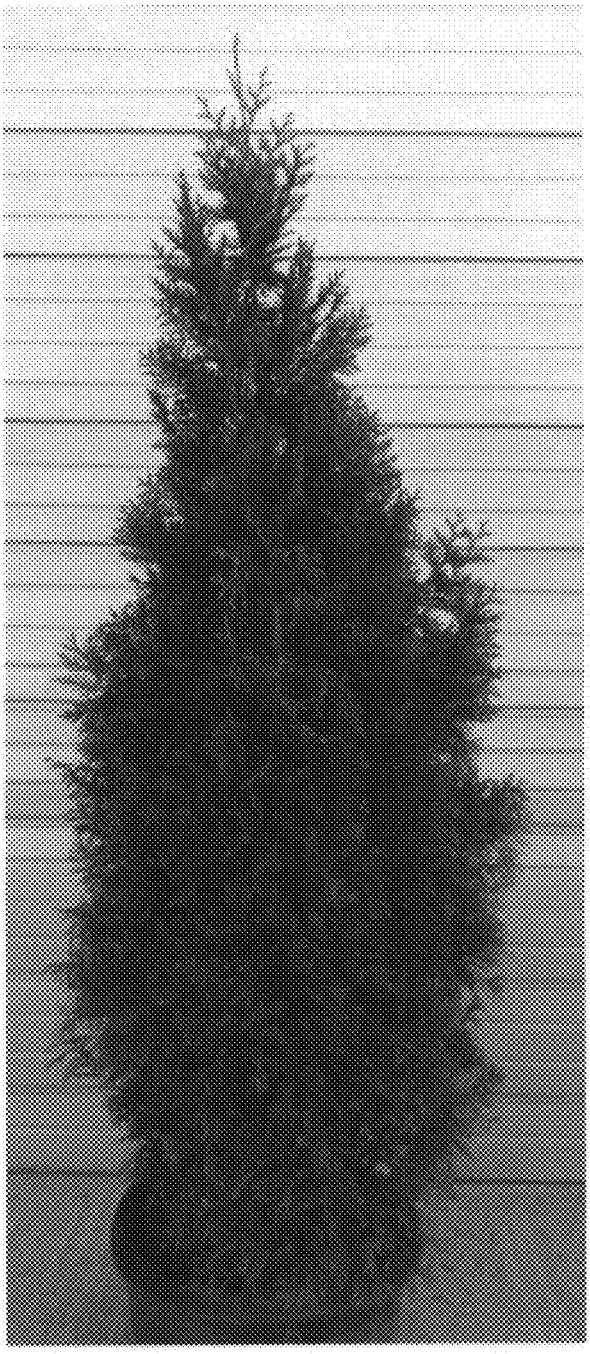

* * * * *